United States Patent [19]

Vermehren et al.

[11] Patent Number: 5,424,480
[45] Date of Patent: Jun. 13, 1995

[54] SUBSTITUTED N-HYDROXYCINNAMAMIDES, PROCESSES FOR THEIR PREPARATION, COMPOSITIONS CONTAINING THEM, AND THEIR USE

[75] Inventors: Jan Vermehren, Idstein/Taunus; Günther Heubach, Kelkheim/Taunus; Peter Braun, Mainz; Burkhard Sachse, Kelkheim/Taunus, all of Germany

[73] Assignee: Hoechst Aktiengesellschaft, Frankfurt am Main, Germany

[21] Appl. No.: 162,858

[22] Filed: Dec. 6, 1993

[30] Foreign Application Priority Data

Dec. 8, 1992 [DE] Germany .................. 42 41 211.0

[51] Int. Cl.$^6$ ............................................ C07C 239/10
[52] U.S. Cl. ................................................ 560/312
[58] Field of Search ...................................... 560/312

[56] References Cited

FOREIGN PATENT DOCUMENTS

74864/81  3/1982  Australia .
0046931   3/1982  European Pat. Off. .
0208999   1/1987  European Pat. Off. .

OTHER PUBLICATIONS

European Abstract No. 46–931.
European Abstract No. 208–999–A.

*Primary Examiner*—José G. Dees
*Assistant Examiner*—Joseph M. Conrad, III
*Attorney, Agent, or Firm*—Curtis, Morris & Safford

[57] ABSTRACT

The invention relates to novel N-alkoxycinnamamides of the formula I

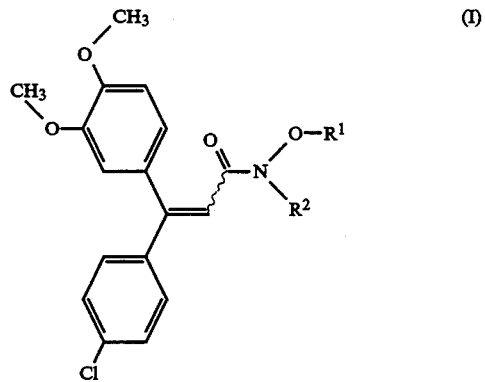

in which $R^1$ and $R^2$ are alkyl, alkenyl, alkynyl, alkoxyalkyl, alkoxyalkenyl, alkoxyalkynyl, trialkylsilylalkynyl or arylalkyl, aryl optionally being substituted by alkyl, alkoxy, haloalkyl, haloalkoxy, alkoxycarbonyl, halogen, cyano, nitro, alkylsulfonyl, phenyl and/or phenoxy, to processes for their preparation, to fungicidal compositions containing them, and to their use as fungicides.

6 Claims, No Drawings

SUBSTITUTED N-HYDROXYCINNAMAMIDES, PROCESSES FOR THEIR PREPARATION, COMPOSITIONS CONTAINING THEM, AND THEIR USE

The invention relates to novel N-alkoxy-cinnamamides of the formula I

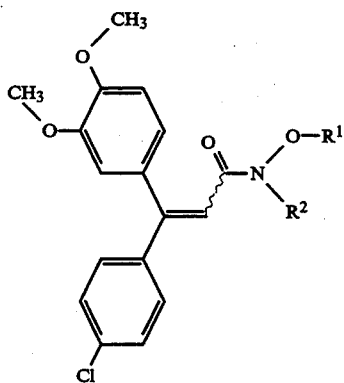

in which $R^1$ and $R'$ are alkyl, alkenyl, alkynyl or optionally substituted arylalkyl, to processes for their preparation, to fungicidal compositions containing them, and to their use as fungicides.

EP-A-208,999 discloses N-alkoxy-cinnamamides, such as N-methoxy-3-(4-methoxy-3-methylphenyl)-N-methylcinnamamide, and their use as fungicides. However, their activity is frequently insufficient.

Novel N-hydroxycinnamamides which have an outstanding fungicidal activity have been found.

The invention therefore relates to compounds of the formula I in which $R^1$ and $R^2$ independently of one another are $C_1$-$C_6$-alkyl, $C_2$-$C_6$-alkenyl, $C_2$-$C_6$-alkynyl, $C_1$-$C_4$-alkoxy-$C_1$-$C_6$-alkyl, $C_1$-$C_4$-alkoxy-$C_2$-$C_6$-alkenyl, $C_1$-$C_6$-alkoxy-$C_2$-$C_6$-alkynyl, tri-($C_1$-$C_1$-alkyl)-silyl-$C_2$-$C_6$-alkynyl or aryl-$C_1$-$C_2$-alkyl, in which aryl is optionally up to tetrasubstituted by identical or different radicals selected from the group comprising $C_1$-$C_4$-alkyl, $C_1$-$C_4$-alkoxy, $C_1$-$C_4$-haloalkyl, $C_1$-$C_4$-haloalkoxy, $C_1$-$C_4$-alkoxycarbonyl, halogen, cyano, nitro, $C_1$-$C_4$-alkylsulfonyl, phenyl and phenoxy.

The alkyl, alkenyl or alkynyl radicals can be straight-chain or branched; the multiple bonds can be terminal or centrally located. The same applies analogously to derived radicals, such as alkoxy and the like. Halogen is F, Cl, Br or I, preferably F, Cl or Br. The prefix "halo" in the name of a substituent is to be understood as meaning here and hereinafter that one or more halogen substituents are possible which can have the same or different meanings. The following may be mentioned as examples of haloalkyl by way of explanation, but not by limitation: $CF_3$, $CHF_2$, $CH_2Br$, $CHCl_2$, $CF_2CHF_2$, $CCl_3$, $CCl_2F$, $CF_2CF_2CF_3$, $CF_2CHFCF_3$, $CH_2CF_3$ and $(CF_2)_3CF_3$. The same applies analogously to derived radicals, such as haloalkoxy.

Aryl preferably represents $C_6$-$C_{12}$-aryl, such as phenyl, naphthyl or biphenylyl, in particular phenyl.

Preferred compounds from amongst those of the formula I are those in which $R^1$ and $R^2$ independently of one another are $C_1$-$C_4$-alkyl, $C_2$-$C_4$-alkenyl, $C_2$-$C_4$-alkynyl, $C_1$-$C_4$-alkoxy-$C_1$-$C_4$-alkyl, $C_1$-$C_4$-alkoxy-$C_2$-$C_4$-alkenyl, $C_1$-$C_4$-alkoxy-$C_2$-$C_4$-alkynyl, tri-($C_1$-$C_2$-alkyl)-silyl-$C_2$-$C_4$-alkynyl or aryl-methyl, aryl optionally being up to tetrasubstituted by identical or different radicals selected from the series comprising $C_1$-$C_4$-alkyl, $C_1$-$C_2$-alkoxy, $C_1$-$C_4$-haloalkyl, $C_1$-$C_2$-haloalkoxy, $C_1$-$C_2$-alkoxycarbonyl, halogen, cyano, nitro, methylsulfonyl, phenyl and phenoxy.

Particularly preferred compounds of the formula I are those in which $R^1$ and $R^2$ independently of one another are $C_1$-$C_2$-alkyl, $C_2$-$C_3$-alkenyl, $C_2$-$C_3$-alkynyl, $C_1$-$C_2$-alkoxy-$C_1$-$C_2$-alkyl, $C_1$-$C_2$-alkoxy-$C_2$-$C_3$-alkenyl, $C_1$-$C_2$-alkoxy-$C_2$-$C_3$-alkynyl, trimethylsilyl-$C_2$-$C_3$-alkynyl or benzyl.

Because of the C=C double bond, the novel compounds of the formula I can be obtained from their preparation in the form of an E/Z isomer mixture, and these isomers can be separated in the customary manner, for example by crystallization or chromatography, to give the individual components. Moreover, some of the compounds of the formula I can have one or more asymmetric carbon atoms or hetero atoms. In such cases, racemates and diastereomers are possible. The invention embraces the pure isomers as well as their mixtures. The mixtures of diastereomers can be separated into the components by conventional methods, for example by selective crystallization from suitable solvents or by chromatography. Racemates can be resolved by conventional methods to give the enantiomers, for example by salt formation with an optically active acid, separation of the diastereomeric salts and liberation of the pure enantiomers by means of a base. The invention embraces the individual isomeric compounds as well as their mixtures, all of which can be used as fungicidal active substances.

The compounds are obtained by processes known per se, by:

a) reacting 3-(4-chlorophenyl)-3-(3,4-dimethoxyphenyl)acrylic acid, of the formula II,

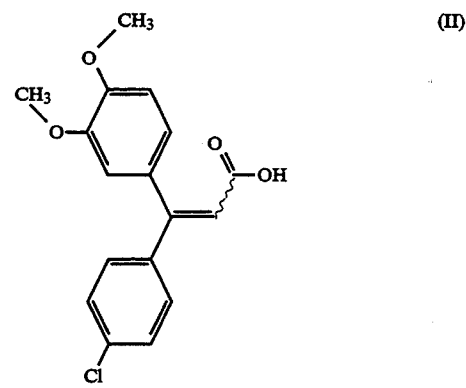

or by reacting a reactive derivative thereof, which may be prepared in situ, with a hydroxyamine derivative of the formula III,

in which $R^1$ and $R^2$ are as defined above. $R^1$ and/or $R^2$ can additionally be hydrogen.

This process is therefore an acylation of a compound of the formula III with a carboxylic acid of the formula II, the reaction being carried out advantageously in the presence of an agent which activates the acid II or in the presence of a dehydrating agent, or else with reactive derivatives of the carboxylic acid of the formula II or of the compound of the formula III.

Suitable derivatives of a carboxylic acid of the formula II which may optionally be prepared in the reaction mixture are, for example, their alkyl, aryl or arylalkyl esters and their methyl, ethyl, phenyl or benzyl esters, their imidazolides, their acid halides, such as the acid chloride or acid bromide, their anhydrides, their mixed anhydrides with aliphatic or aromatic carboxylic or sulfonic acids or with carboxylic esters, for example with acetic acid, propionic acid, p-toluenesulfonic acid or O-ethyl- or O-isobutyl carbonic acid, or their N-hydroximidates.

Suitable acid-activating and/or dehydrating agents are, for example, a chlorocarbonic ester, such as ethyl chloroformate, isobutyl chloroformate, phosphorus pentoxide, N,N'-dicyclohexylcarbodiimide, N,N'-carbonyldiimide, N,N'-carbonyldiimidazole or N,N'-thionyldiimide.

The reaction is expediently carried out in an inert solvent or solvent mixture, such as methylene chloride, chloroform, carbon tetrachloride, ether, tetrahydrofuran, dioxane, benzene, toluene, acetonitrile, N-methylpyrrolidine or dimethylformamide, if appropriate in the presence of an inorganic base, such as sodium carbonate, or of a tertiary organic base, such as triethylamine, N-methylmorpholine or pyridine, it also being possible for this base to act simultaneously as the solvent, and, if appropriate, in the presence of an acid-activating agent, at temperatures between −78° C. and 120° C., but preferably at temperatures between −78° C. and the boiling point of the reaction mixture. It is not necessary for a reactive derivative of a compound of the formula II or III, which may have formed in the reaction mixture, to be isolated; furthermore, the reaction can also be carried out in an excess of the compound of the formula III which has been employed, to act as a solvent.

If desired, mixtures of E/Z isomers which have been obtained according to the invention can subsequently be separated by customary methods to give the corresponding E and Z isomers.

b) Compounds of the formula I can also be synthesized by reacting a ketone of the formula IV with a phosphonacetamide of the formula V

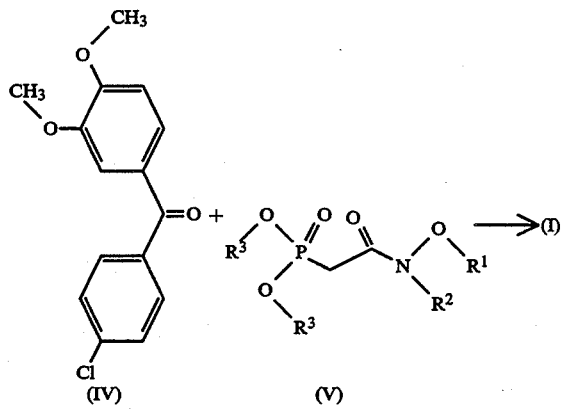

in which $R^1$ and $R^2$ are as defined above and $R^3$ is an aliphatic radical, preferably a lower alkyl radical, in particular having up to 6 carbon atoms, by the method of Wittig and Horner.

Compound IV has been disclosed in DE-A-3,643,403.

c) Compounds of the formula I can also be synthesized by reacting an N-alkoxycinnamamide of the formula VI with an alkylating agent of the formula VII, the radicals $R^1$ and $R^2$ being as defined above and X being halogen or alkoxysulfonyl, preferably having up to 6 carbon atoms, in the presence of a base, such as alkali metal hydrides, in particular sodium hydride, or an alkali metal alcoholate, such as potassium tert-butylate.

The reaction is expediently carried out in a solvent or solvent mixture, such as methylene chloride, chloroform, carbon tetrachloride, ether, tetrahydrofuran, dioxane, benzene, toluene, acetonitrile, N-methylpyrrolidine or dimethylformamide, at temperatures between −40° C. and 180° C, preferably between −40° C. and the boiling point of the reaction mixture.

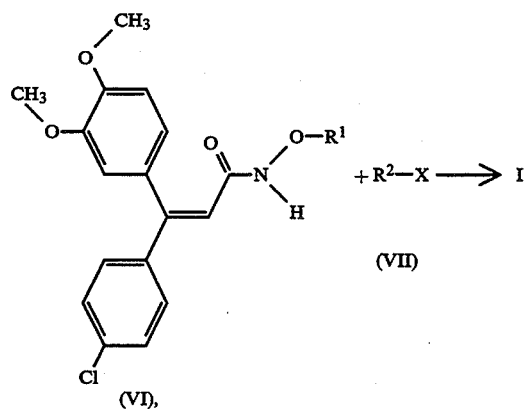

The compounds of the formula VI can be prepared as described for route a).

d) Compounds of the formula I can also be prepared by reacting a ketone of the formula IV with an acethydroxamic acid derivative of the general formula IX, the radicals $R^1$ and $R^2$ being as defined above, in the presence of a strong base.

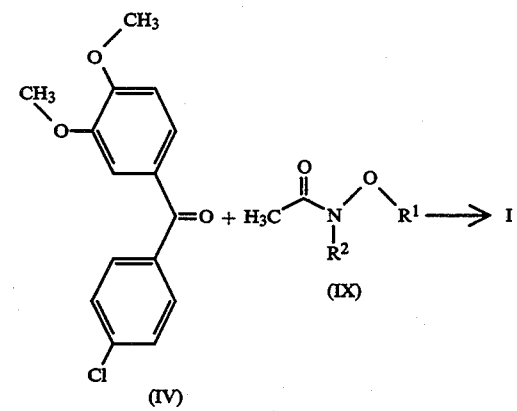

Examples of suitable bases are metal hydroxides, metal carbonates, metal alcoholates and metal salts of monoalkyl carbonates, or mixtures of these bases. The reaction is expediently carried out in an inert diluent, such as toluene, xylene, diethyl ether, tetrahydrofuran, diglyme, N,N-dimethylformamide or N-methylpyrrolidone. Depending on the reactivity of the reagents, the reaction can be carried out at temperatures between 25° C. and the boiling point of the reaction mixture. It may be advantageous to use an excess of 1 to 3 times the amount of base, and an excess of 1 to 3 times the amount of the compound of the formula IX also has a favorable effect on the reaction.

The compounds of the formula I according to the invention are distinguished by an outstanding fungicidal activity. They can be used for successfully controlling, in a curative manner, fungal pathogens which have already penetrated the plant tissue. This is particularly important and advantageous in the case of those fungal diseases which can no longer be controlled effectively with the conventional fungicides once infection has taken place. The spectrum of action of the compounds claimed embraces a range of economically important phytopathogenic fungi, such as *Phytophthora infestans* and *Plasmopara viticola*.

Besides, the compounds according to the invention are suitable for use in various technical fields, for example as wood preservatives, as preservatives in paints, in cooling lubricants for metal working, or as preservatives in drilling and cutting oils.

The invention also relates to compositions which contain the compounds of the formula I besides suitable formulation auxiliaries. The compositions according to the invention generally contain 1 to 95% by weight of the active substances of the formula I.

They can be formulated in various ways, depending on the prevailing biological and/or chemico-physical parameters. The following are therefore suitable possibilities for formulation: wettable powders (WP), emulsifiable concentrates (EC), aqueous dispersions on oil or water bases (SC), suspoemulsions (SC), dusts (DP), seeds-dressing products, granules in the form of water-dispersible granules (WG), ULV formulations, microcapsules, waxes or baits.

These individual types of formulation are known in principle and are described, for example, in: Winnacker-Küchler, "Chemische Technologie", [Chemical Technology], Volume 7, C. Hauser Verlag, Munich, 4th Ed. 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carrier", 2nd Ed., Darland Books, Caldwell N.J.; H. v. Olphen, "Introduction to Clay Colloid Chemistry, 2nd Ed., J Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schöfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active substances, fertilizers and/or growth regulators, for example in the form of a readymix or a tank mix.

Wettable powders are preparations which are uniformly dispersible in water and which contain, besides the active substance, wetting agents, for example polyoxethylated alkylphenols, polyoxethylated fatty alcohols, alkyl- or alkylphenol sulfonates, and dispersants, for example sodium lignosulfonate, sodium 2,2'-dinaphthylmethane-6,6'-disulfonate, sodium dibutylnaphthalenesulfonate or else sodium oleylmethyltaurate, in addition to a diluent or inert substance. Emulsifiable concentrates are prepared by dissolving the active substance in an organic solvent, for example butanol, cyclohexanone, dimethylformamide, xylene or else higher-boiling aromatics or hydrocarbons, with an addition of one or more emulsifiers. The following are examples of substances which can be used as emulsifiers:

Calcium salts of alkylarylsulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyether, sorbitan fatty acid esters, polyoxyethylene sorbitan fatty acid esters or polyoxyethylene sorbitol esters.

Dusts are obtained by grinding the active substance with finely divided solid substances, for example talc, natural clays, such as kaolin, bentonite or pyrophyllite, or diatomaceous earth. Granules can be prepared either by spraying the active substance onto adsorptive, granulated inert material, or by applying active substance concentrates to the surface of carriers, such as sand, kaolinites or granulated inert material, by means of binders, such as polyvinyl alcohol, sodium polyacrylate or else mineral oils. Suitable active substances can also be granulated in the manner customary for the preparation of fertilizer granules, if desired in the form of a mixture with fertilizers.

The active substance concentration in wettable powders is, for example, approximately 10 to 90% by weight, the remainder to 100% by weight being composed of conventional formulation constituents. In the case of emulsifiable concentrates, the active substance concentration can be from approximately 5 to 80% by weight. Formulations in the form of dusts contain in most cases 5 to 20% by weight of active substance. In the case of granules, the active substance content depends partly on whether the active compound is in liquid or solid form and on which granulation auxiliaries, fillers and the like are used.

Besides, the active substance formulations which have been mentioned may contain, if appropriate, the adhesives, wetting agents, dispersants, emulsifiers, penetrants, solvents, fillers or carriers which are conventional in each case.

For use, the concentrates, which are in commercially available form, are, if appropriate, diluted in the customary manner, for example by means of water in the case of wettable powders, emulsifiable concentrates, dispersions and, in some cases, also in the case of microgranules.

Preparations in the form of dusts and granulated preparations and sprayable solutions are conventionally not further diluted with other inert substances before they are used.

The application rate required varies with the external conditions such as, inter alia, temperature and humidity. It can vary within wide limits, for example between 0.005 and 10.0 kg/ha or more of active ingredient, but it is preferably between 0.01 and 5 kg/ha.

The active substances according to the invention can be applied in their commercially available formulations, either by themselves or in combination with other fungicides known from the literature.

Products which must be mentioned as fungicides which are known from the literature and which can be combined according to the invention with the compounds of the formula I are, for example, the following:

aldimorph, andoprim (PM213), anilazine, BAS 480F, BAS 490F, benalaxyl, benodanil, benomyl, binapacryl, bitertanol, bromuconazole, buthiobate, captafol, captan, carbendazime, carboxin, CGA 173506, chlobenzothiazone, chlorthalonil, cymoxanil, cyproconazole, cyprofuram, dichlofluanid, dichlomezin, diclobutrazol, diethofencarb, difenconazole, (CGA 169374), difluconazole, dimethirimol, dimethomorph, diniconazole, dinocap, dithianon, dodemorph, dodine, edifenfos, ethirimol, etridiazole, fenarimol, fenfuram, fenpiclonil, fenpropidin, fenpropimorph, fentin acetate, fentin hydroxide, fluazinam, fluobenzimine, fluquinconazole, fluorimide, flusilazole, flutolanil, flutriafol, folpet, fosetyl-aluminum, fuberidazole, fulsulfamide, furalaxyl, furconazole (LS 840606), furmecyclox, guazatine, hexaconazole, ICI A 5504, imazalil, imibenconazole, iprobenfos, iprodione, isoprothiolane, copper compounds, such as copper oxychloride, oxine-copper, copper oxide, mancozeb, maneb, mepanipyrim, metconazole, mepronil, metalaxyl, methasulfocarb, methfuroxam, myclobutanil, nabam, nitrothalidopropyl, nuarimol, ofurace, oxadixyl, oxycarboxin, penconazole, pencycuron, PP 969, probenazole, propineb, prochloraz, procymidone, propamocarb, propiconazole, prothiocarb, pyracarbolid, pyrazophos, pyrifenox, pyroquilon, rabenzazole, RH 7592, sulfur, tebuconazole, TF 167, thiabendazole, thicyofen, thiophanate-methyl, thiram, tolclofos-methyl, tolylfluanid, triadimefon, triadimenol, tricyclazole, tridemorph, triflumizole, triforine, validamycin, vinchlozoline, zineb, sodium dodecylsulfonate, sodium dodecyl sulfate, sodium C13/C15-alcohol ether sulfonate, sodium cetostearyl phosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkylimidazoline.

The abovementioned components for mixtures are known active substances, many of which being described in CH.R Worthing, U.S.B. Walker, The Pesticide Manual, 7th Edition (1983), British Crop Protection Council.

Moreover, the active substance according to the invention, and its commercially available formulations and in the use forms prepared with these formulations, can exist in the form of a mixture with other active substances, such as insecticides, attractants, sterilants, acaricides, nematicides or herbicides. The insecticides include, for example, phosphoric esters, carbamates, carboxylic esters, formamidines, tin compounds, substances produced by microorganisms and the like. Preferred components for mixtures are:

1. From the group of the phosphorus compounds acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, 0,0-1,2,2,2-tetrachloroethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemetonmethyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion.

2. From the group of the carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa7-oxo-5,11-dithia-9-dodecenoate (OK 135), 1-methylthio(ethylideneamino)-N-methyl-N-(morpholinothio)carbamate (UC 51717).

3. From the group of the carboxylic esters allethrin, alphamethrin, 5-benzyl-3-furylmethyl (E)-(1R)-cis-2,2-di-methyl-3-(2-oxothiolan-3-ylidenemethyl)cyclopropanecarboxylate, bioallethrin, bioallethrin ((S)-cyclopentyl isomer), bioresmethrin, biphenate, (RS)-1-cyano-1-(6-phenoxy-2-pyridyl)-methyl (1RS)-trans-3-(4-tert.butylphenyl)-2,2-dimethylcyclopropanecarboxylate (NCl 85193), cycloprothrin, cyhalothrin, cypermethrin, cyphenothrin, deltamethrin, empenthrin, esfenvalerate, fenfluthrin, fenpropathrin, fenvalerate, fenfluthrin, fenpropathrin, fenvalerate, flucythrinate, flumethrin, fluvalinate (D isomer), permethrin, pheothrin ((R) isomer), d-pralethrin, pyrethrins (natural products), resmethrin, tefluthrin, tetramethrin, tralomethrin.

4. From the group of the amidines amitraz, chlordimeform

5. From the group of the tin compounds cyhexatin, fenbutatin oxide

6. Others abamectin, Bacillus thuringiensis, bensultap, binapacryl, bromopropylate, buprofezin, camphechlor, cartap, chlorobenzilate, chlorfluazuron, 2-(4-(chlorophenyl)-4,5-diphenylthiophene (UBl-T 930), chlorfentezine, 2-naphthylmethyl cyclopropanecarboxylate (Ro12-0470), cyromazin, ethyl N-(3,5-dichloro-4-(1,1,2,3,3,3-hexafluoro-1propyloxy)phenyl)carbamoyl)-2-chlorobenzocarboximidate, DDT, dicofol, N-(N-(3,5-di-chloro-4-(1,1,2,2-tetrafluoroethoxy)phenylamino)carbonyl)-2,6-difluorobenzamide (XRD 473), diflubenzuron, N-(2,3-dihydro-3-methyl)-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramechylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinon-3-ylcarbamaldehyde (WL 108477), propargite, teflubenzuron, tetradifon, tetrasul, thiocyclam, triflumuron.

The active substance content of the use forms prepared with the commercially available formulations can vary within wide limits, and the active substance concentration of the use forms can be from 0.0001 up to 95% by weight of active substance, preferably between 0.001 and 1% by weight. They are applied in the customary manner which has been adapted to suit one of the use forms.

The examples which follow are intended to illustrate the invention, but not by way of limitation.

A. Formulation examples a) A dust is obtained by mixing 10 parts by weight of active substance and 90 parts by weight of talc as inert substance and comminuting the mixture in a hammer mill.

b) A wettable powder which is readily dispersible in water is obtained by mixing 25 parts by weight of active substance, 65 parts by weight of kaolin-containing quartz as inert substance, 10 parts by weight of potassium lignosulfonate and 1 part by weight of sodium oleoylmethyltaurate as wetting and dispersing agent, and grinding the mixture in a pinned-disk mill.

c) A dispersion concentrate which is readily dispersible in water is prepared by mixing 40 parts by weight of active substance with 7 parts by weight of a sulfosuccinate monoester, 2 parts by weight of a sodium lignosulfonate and 51 parts by weight of water, and grinding the mixture in a ball mill to a fineness of below 5 microns.

d) An emulsifiable concentrate can be prepared with 15 parts by weight of active substance, 75 parts by weight of cyclohexanone as solvent and 10 parts by weight of oxethylated nonylphenol (10 EO) as emulsifier.

e) Granules can be prepared with 2 to 15 parts by weight of active substance and an inert carrier material for granules, such as attapulgite, pumice granules and/or quartz sand. It is expedient to use a suspension of the wettable powder of Example b) with a solids content of 30%, which is sprayed onto the surface of attapulgite granules, and this is dried and mixed intimately. The amount of the wettable powder is approximately 5% by weight, and the amount of inert carrier material about 95% by weight, of the finished granules.

C. Chemical examples

EXAMPLE 1

3-(4-Chlorophenyl)-3-(3,4-dimethoxyphenyl)-N-methoxy-N-methylacrylamide 7.3 ml of N-methylmorpholine were added to a solution of 10.0 g of 3-(4-chlorophenyl)-3-(3,4-dimethoxyphenyl)acrylic acid in 100 ml of tetrahydrofuran. The mixture was subsequently cooled to $-15°$ C., and 3.35 ml of ethyl chloroformate were added dropwise. The mixture was stirred for 20 minutes at this temperature and subsequently cooled to $-60°$ C., and 3.07 g of N,O-dimethylhydroxylamine hydrochloride were added. The mixture was stirred for 2 hours at $-60°$ C. and then allowed to come to room temperature. The mixture was poured into aqueous ammonium chloride solution, this was extracted several times using ether, and the organic phases were washed using saturated NaCl solution and dried over magnesium sulfate. The solvent was evaporated in vacuo, and the residue was purified by chromatography (eluent ethyl acetate). 3.8 g of one diastereomer (1a) and 1.4 g of the other diastereomer (1b) were obtained in the form of colorless oils.

$^1$H-NMR (CDCl$_3$): 6.67 ppm (olefin-H), 1a 6.53 ppm (olefin-H), 1b

The absolute stereochemistry of the isomers can be determined with the aid of NMR spectroscopy with the aid of the nuclear Overhauser effect (The Nuclear Overhauser Effect, J. H. Noggle, R. E. Schirmer, Academic Press New York and London 1971). The result is that the absolute configuration "E" can be assigned to the isomer 1a, and the absolute configuration "Z" to the isomer 1b.

The compounds of Table 1 are prepared analogously.

TABLE 1

| Example No. | R$^1$ | R$^2$ | Physical data N$^D_{30}$/m.p. |
|---|---|---|---|
| 1a (E) | CH$_3$ | CH$_3$ | 1.5830 |
| 1b (Z) | CH$_3$ | CH$_3$ | 1.5480 |
| 2 | CH$_3$ | C$_2$H$_5$ | 1.5825 |
| 3 | CH$_3$ | n-C$_3$H$_7$ | |
| 4 | CH$_3$ | n-C$_4$H$_9$ | |
| 5 | CH$_3$ | CH$_2$—CH$_2$—OCH$_3$ | |
| 6 | CH$_3$ | CH$_2$—CH$_2$—O—C$_2$H$_5$ | |
| 7 | CH$_3$ | CH$_2$—CH=CH$_2$ | wax |
| 8 | CH$_3$ | CH$_2$—CH=CH—CH$_3$ | |
| 9 | CH$_3$ | CH$_2$—CH=CH—OCH$_3$ | |
| 10 | CH$_3$ | CH$_2$—C(OCH$_3$)=CH$_2$ | |
| 11 | CH$_3$ | CH$_2$—C≡CH | 1.5950 |
| 12 | CH$_3$ | CH$_2$—C≡C—Si(CH$_3$)$_3$ | |
| 13 | CH$_3$ | CH$_2$—C≡C—CH$_3$ | |
| 14 | CH$_3$ | CH(CH$_3$)—C≡CH | |
| 15 | CH$_3$ | CH$_2$—C$_6$H$_5$ | 1.6050 |
| 16 | CH$_3$ | CH$_2$—C$_6$H$_4$-4-CH$_3$ | |
| 17 | CH$_3$ | CH$_2$—C$_6$H$_4$-4-F | |
| 18 | CH$_3$ | CH$_2$—C$_6$H$_4$-2-Cl | |
| 19 | CH$_3$ | CH$_2$—C$_6$H$_3$—3,4-(Cl)$_2$ | |
| 20 | CH$_3$ | CH$_2$—C$_6$H$_4$-4-OCH$_3$ | |
| 21 (Z) | C$_2$H$_5$ | CH$_3$ | 1.5751 |
| 22 | C$_2$H$_5$ | C$_2$H$_5$ | |
| 23 (Z) | C$_2$H$_5$ | CH$_2$—CH=CH$_2$ | 1.5830 |

TABLE 1-continued

| Example No. | $R^1$ | $R^2$ | Physical data $N^D_{30}$/m.p. |
|---|---|---|---|
| 24 | $C_2H_5$ | $CH_2-CH=CH-OCH_3$ | |
| 25 | $C_2H_5$ | $CH_2-C\equiv C-H$ | 1.5920 |
| 26 | $C_2H_5$ | $CH_2-C\equiv C-Si(CH_3)_3$ | |
| 27 | $C_2H_6$ | $CH_2-C_6H_4-4-SO_2CH_3$ | |
| 28 | $C_2H_5$ | $CH_2-C\equiv C-CH_2-OCH_3$ | |
| 29 | $C_2H_5$ | $CH(CH_3)-C_6H_5$ | |
| 30 | $CH_2CF_3$ | $CH_3$ | |
| 31 | $CH_2CF_3$ | $CH_2CF_3$ | |
| 32 | $CH_2CF_3$ | $CH_2-CH=CH_2$ | |
| 33 | $CH_2CF_3$ | $CH_2-C_6H_4-3-O-C_6H_5$ | |
| 34 | $CH_2CF_3$ | $CH_2-C_6H_4-3-CF_3$ | |
| 35 | $CH_2CF_3$ | $CH_2-CH_2-OCH_3$ | Oil |
| 36 | $CF_2-CHF_2$ | $CH_2-CH_2-O-C_2H_5$ | |
| 37 | $CF_2-CHF_2$ | $CH_3$ | |
| 38 | $CF_2-CHF_2$ | $CF_2-CHF_2$ | |
| 39 | $CF_2-CHF_2$ | $CH_2-C_6H_5$ | |
| 40 | $CF_2-CHF_2$ | $CH_2-CH=CH_2$ | |
| 41 | $n-C_3H_7$ | $CH_3$ | |
| 42 | $n-C_3H_7$ | $C_2H_5$ | |
| 43 | $n-C_3H_7$ | $CH_2CH(CH_3)_2$ | |
| 44 | $n-C_3H_7$ | $CH_2-CH=CH_2$ | |
| 45 | $n-C_3H_7$ | $CH_2-C\equiv C-Si(CH_3)_3$ | |
| 46 | $n-C_3H_7$ | $n-C_3H_7$ | |
| 47 | $n-C_3H_7$ | $CH(CH_3)-C_6H_5$ | |
| 48 | $n-C_4H_9$ | $CH_3$ | |
| 49 | $n-C_4H_9$ | $n-C_4H_9$ | |
| 50 | $n-C_4H_9$ | $CH_2-CH(CH_3)_2$ | |
| 51 | $n-C_4H_9$ | $CH_2-CH=CH_2$ | |
| 52 | $n-C_4H_9$ | $CH_2-C\equiv C-CH_3$ | |
| 53 | $n-C_4H_9$ | $CH_2-C_6H_4-2-Br$ | |
| 54 | $n-C_4H_9$ | $CH_2-C_6H_3-2,4-F_2$ | |
| 55 | $i-C_4H_9$ | $CH_3$ | |
| 56 | $i-C_4H_9$ | $C_2H_5$ | |
| 57 | $i-C_4H_9$ | $i-C_4H_9$ | |
| 58 | $i-C_4H_9$ | $CH_2-C_6H_5$ | |
| 59 | $CH_2-OCH_3$ | $CH_3$ | |
| 60 | $CH_2-OCH_3$ | $C_2H_5$ | |
| 61 | $CH_2-OCH_3$ | $CH_2-CH=CH_2$ | |
| 62 | $CH_2-OCH_3$ | $CH_2-C\equiv CH$ | |
| 63 | $CH_2-OCH_3$ | $CH_2-C_6H_5$ | |
| 64 | $CH_2-OCH_3$ | $CH_2-OCH_3$ | |
| 65 | $CH_2-OCH_3$ | $CH_2F$ | |
| 66a (E) | $CH_2-CH=CH_2$ | $CH_3$ | 1.5889 |
| 66b (Z) | $CH_2-CH=CH_2$ | $CH_3$ | 1.5878 |
| 67a (E) | $CH_2-CH=CH_2$ | $C_2H_5$ | resin |
| 67b (Z) | $CH_2-CH=CH_2$ | $C_2H_5$ | resin |
| 68 | $CH_2-CH=CH_2$ | $n-C_3H_7$ | |
| 69 | $CH_2-CH=CH_2$ | $CH_2-CH(CH_3)_2$ | |
| 70a (E) | $CH_2-CH=CH_2$ | $CH_2-CH=CH_2$ | 1.5904 |
| 70b (Z) | $CH_2-CH=CH_2$ | $CH_2-CH=CH_2$ | 1.5714 |
| 71 | $CH_2-CH=CH_2$ | $CH_2-C\equiv C-Si(CH_3)_3$ | |
| 72 (E/Z) | $CH_2-CH=CH_2$ | $CH_2-C_6H_5$ | 1.5932 |
| 73 | $CH_2-CH=CH_2$ | $CH_2-C_6H_4-3-F$ | |
| 74 | $CH_2-CH=CH_2$ | $CH_2-C_6H_4-3-OC_6H_5$ | |
| 75 | $CH_2-CH=CH_2$ | $CH_2-C_6H_4-4-OCH_3$ | |
| 76 | $CH_2-CH=CH_2$ | $CH_2-C_6H_4-3-CF_3$ | |
| 77 | $CH_2-CH=CH_2$ | $CH_2-C_6H_4-4-Cl$ | |
| 78 | $CH_2-CH=CH_2$ | $CH_2-C_6H_3-2,4-Cl_2$ | |
| 79 | $CH_2-CH=CH_2$ | $CH_2-C_2H-2,3,5,6-F_4$ | |
| 80 | $CH_2-CH=CH_2$ | $CH_2-C_6F_4-4-CH_3$ | |
| 81 | $CH_2-C\equiv CH$ | $CH_3$ | |
| 82 | $CH_2-C\equiv CH$ | $C_2H_5$ | |
| 83 | $CH_2-C\equiv CH$ | $CH_2-C\equiv CH$ | |
| 84 | $CH_3-C\equiv CH$ | $CH_2-C_6H_5$ | |
| 85 | $CH_2-C\equiv CH$ | $CH_2OCH_3$ | |
| 86 | $CH_2-C\equiv CH$ | $CH_2OCH_2-CH_2-CH_3$ | |
| 87 | $CH_2-c\equiv CH$ | $CH_2CH_2OC_2H_5$ | |
| 88 | $CH_2-C\equiv C-Si(CH_3)_3$ | $CH_3$ | |
| 89 (E/Z) | $CH_2-C_6H_5$ | $CH_3$ | 102-103° C. |
| 90 | $CH_2-C_6H_5$ | $CHF_2$ | |
| 91 | $CH_2-C_6H_5$ | $CH_2Cl$ | |
| 92 (E/Z) | $CH_2-C_6H_5$ | $CH_2-CH=CH_2$ | resin |
| 93 | $CH_2-C_6H_5$ | $CH(CH_3)-CH=CH_2$ | |
| 94 | $CH_2-C_6H_5$ | $CH_2-C(CH_3)=CH_2$ | |
| 95 | $CH_2-C_6H_5$ | $CH_2-C\equiv CH$ | |
| 96 (E/Z) | $CH_2-C_6H_5$ | $C_2H_5$ | resin |
| 97 | $CH_2-C_6H_5$ | $n-C_3H_7$ | |
| 98 | $CH_2-C_6H_5$ | $i-C_3H_7$ | |

TABLE 1-continued

| Example No. | $R^1$ | $R^2$ | Physical data $N^D{}_{30}$/m.p. |
|---|---|---|---|
| 99 | $CH_2-C_6H_5$ | $CH_2CF_3$ | |
| 100 | $CH_2-C_6H_5$ | $CF_2-CHF-CF_3$ | |
| 101 | $CH_2-C_6H_4-4-F$ | $CH_3$ | |
| 102 | $CH_2-C_6H_4-4-F$ | $CH_2-CH-CH_2$ | |
| 103 | $CH_2-C_6H_4-4-F$ | $CH_2-C\equiv CH$ | |
| 104 | $CH_2-C_6H_4-4-F$ | $CH_2-C_6H_4-4-F$ | |
| 105 | $CH_2-C_6H_4-4-OCH_3$ | $CH_3$ | |
| 106 | $CH_2-C_6H_4-4-OCH_3$ | $C_2H_5$ | |
| 107 | $CH_2-C_6H_4-4-OCH_3$ | $CH_2-C_6H_5$ | |
| 108 | $CH_2-C_6H_4-3-CF_3$ | $CH_3$ | |
| 109 | $CH_2-C_6H_4-3-CF_3$ | $CH_2-CH_2-OC_2H_5$ | |
| 110 | $CH_2-C_6H_4-4-CH_3$ | $CH_3$ | |
| 111 | $CH_2-C_6H_4-4-CH_3$ | $CH_2-C_6H_4-4-CH_3$ | |
| 112 | $CH_2-C_6H_4-4-SO_2CH_3$ | $CH_3$ | |
| 113 | $CH_2-C_6H_4-4-SO_2CH_3$ | $C_2H_5$ | |
| 114 | $CH_2-C_6H_4-4-COOC_2H_5$ | $CH_3$ | |
| 115 | $CH_2-C_6H_4-4-COOC_2H_5$ | $CH_2-C_6H_4-4-COOC_2H_5$ | |
| 116 | $CH_2-C_6H_3-4-Cl-3-F$ | $CH_3$ | |
| 117 | $CH_2-C_6H_3-3-Cl-4-F$ | $CH_2-C_6H_3-3-Cl-4-F$ | |
| 118 | $CH_2-C_6F_4H$ | $CH_2C_6F_4H$ | |
| 119 | $CH_2-C_6F_4-4-CH_3$ | $CH_2-C_6F_4-4-CH_3$ | |
| 120 | $CH_2-C_6H_4-2-CN$ | $CH_3$ | |

C. Biological examples

N-Methoxy-3-(4-methoxy-3-methylphenyl)-N-methylcinnamamide, of the formula VIII, was used as comparative substance.

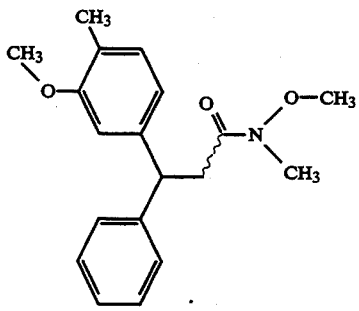

VIII

Example 1

*Phytophthora infestans*

Tomato plants cv. "Rheinlands Ruhm" in the 3- to 4-leaf stage were wetted uniformly to run off point with aqueous suspensions of the claimed compounds. After the mixture had dried, the plants were inoculated with a zoosporangia suspension of Phytophthora infestans and kept for 2 days in a controlled-environment chamber under ideal conditions for infection. After this, the plants were grown on in the greenhouse until they showed the symptoms. The disease level was scored about 1 week after inoculation. The disease level of the plants was expressed in % of diseased leaf area in comparison with the untreated controlled plants, whose infection level was 100%. The following substances suppressed disease completely at a concentration of 500 mg of active substance/l of spray mixture:

1a, 1b

In comparison, VIII shows no activity.

Example 2

*Plasmopara viticola*

Approx. 6 weeks after sowing, grape seedlings cvs. "Riesling/Ehrenfelder" were treated to run off point with aqueous suspensions of the claimed compounds. After the spray coating had dried, the plants were inoculated with a zoosporangia suspension of Plasmopara viticola, and the dripping wet plants were placed for 4–5 hours into a controlled-environment cabinet at 23° C. and a relative atmospheric humidity of 80–90%.

After an incubation time of 7 days in the greenhouse, the plants were returned overnight into the controlled-environment cabinet to stimulate sporulation of the fungus. The disease level was subsequently evaluated. The disease level was expressed in % of diseased leaf area in comparison with the untreated controlled plants whose disease level was 100%.

The following substances suppressed disease completely at a concentration of 500 mg of active substance/l of spray mixture:

1a, 1b

In comparison, VIII shows no activity.

We claim:

1. A compound of the formula I

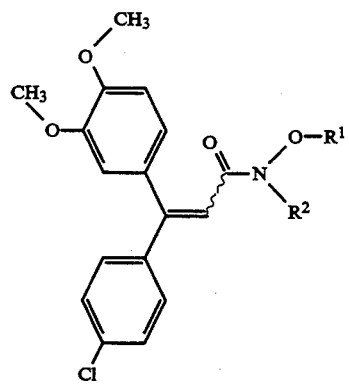

(I)

in which $R^1$ and $R^2$ independently of one another are $C_1-C_6$-alkyl, $C_2-C_6$-alkenyl, $C_2-C_6$-alkynyl, $C_1-C_4$-alkoxy-$C_1-C_6$-alkyl, $C_1-C_4$-alkoxy-$C_2-C_6$-alkenyl, $C_1-C_4$-alkoxy-$C_2-C_6$-alkynyl, or aryl-$C_1-C_2$-alkyl, in which aryl is optionally up to tetrasubstituted by identical or different radicals selected from the group comprising $C_1-C_4$-alkyl, $C_1-C_4$-alkoxy, $C_1-C_4$-haloalkyl, $C_1-C_4$-haloalkoxy, $C_1-C_4$-alkoxycarbonyl, halogen, cyano, nitro, $C_1-C_4$-alkylsulfonyl, phenyl and phenoxy.

2. A compound of the formula I as claimed in claim 1, in which $R^1$ and $R^2$ independently of one another are $C_1$–$C_4$-alkyl, $C_2$–$C_4$-alkenyl, $C_2$–$C_4$-alkynyl, $C_1$–$C_4$-alkoxy-$C_1$–$C_4$-alkyl, $C_1$–$C_4$-alkoxy-$C_2$–$C_4$-alkenyl, $C_1$–$C_4$-alkoxy-$C_2$–$C_4$-alkynyl, or arylmethyl, aryl optionally being up to tetrasubstituted by identical by different radicals selected from the series comprising $C_1$–$C_4$-alkyl, $C_1$–$C_2$-alkoxy, $C_1$–$C_4$-haloalkyl, $C_1$–$C_2$-haloalkoxy, $C_1$–$C_2$-alkoxycarbonyl, halogen, cyano, nitro, methylsulfonyl, phenyl and phenoxy.

3. A compound of the formula I as claimed in claim 1, in which $R^1$ and $R^2$ independently of one another are $C_1$–$C_2$-alkyl, $C_2$–$C_3$-alkenyl, $C_2$–$C_3$-alkynyl, $C_1$–$C_2$-alkoxy-$C_1$–$C_2$-alkyl, $C_1$–$C_2$-alkoxy-$C_2$–$C_3$-alkenyl, $C_1$–$C_2$-alkoxy-$C_2$–$C_3$-alkynyl, or benzyl.

4. A fungicidal composition containing a fungicidally effective amount of at least one compound as claimed in claim 1 together with the additives or auxiliaries which are customary for its use.

5. A crop protection product as claimed in claim 4, containing a fungicidally effective amount of at least one compound as claimed in claim 1 and at least one further active substance, selected from the group consisting of fungicides, insecticides, attractants, sterilants, acaricides, nematicides and herbicides, together with the auxiliaries and additives which are customary for such a use.

6. A composition as claimed in claim 4 for use in the protection of wood or as a preservative in paints, in cooling lubricants for metal working or in drilling and cutting oils, containing an effective amount of at least one compound as claimed in claim 1 together with the auxiliaries and additives customary for such uses.

* * * * *

UNITED STATES PATENT AND TRADEMARK OFFICE
CERTIFICATE OF CORRECTION

PATENT NO. : 5,424,480
DATED : June 13, 1995
INVENTOR(S) : Vermehren et al

It is certified that error appears in the above-indentified patent and that said Letters Patent is hereby corrected as shown below:

In column 13, formula VIII, instead of a single bond insert a double bond as indicated by the yellow highlighted area below.

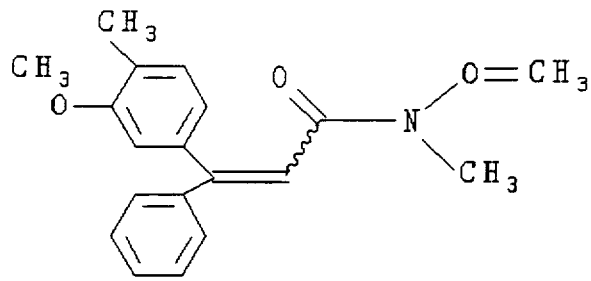

Signed and Sealed this

Seventeenth Day of October, 1995

Attest:

BRUCE LEHMAN

Attesting Officer

Commissioner of Patents and Trademarks